United States Patent [19]
Schlesinger et al.

[11] Patent Number: 5,026,686
[45] Date of Patent: Jun. 25, 1991

[54] ANTIVIRAL PEPTIDES

[75] Inventors: Milton J. Schlesinger, St. Louis; Steven P. Adams, St. Charles, both of Mo.

[73] Assignee: Washington University, St. Louis, Mo.

[21] Appl. No.: 305,148

[22] Filed: Feb. 1, 1989

[51] Int. Cl.$^5$ .................. A61K 37/02; C07K 5/10; C07K 7/06

[52] U.S. Cl. .................. 514/17; 424/88; 424/89; 424/101; 514/8; 514/15; 514/16; 514/18; 530/322; 530/328; 530/329; 530/330

[58] Field of Search .................. 424/88, 89, 101; 530/328-330, 322; 514/17, 18, 8, 13-16

[56] References Cited

U.S. PATENT DOCUMENTS

| | | | |
|---|---|---|---|
| 4,481,189 | 11/1984 | Prince | 424/101 |
| 4,540,573 | 9/1985 | Neurath et al. | 424/101 |
| 4,554,101 | 11/1985 | Hopp | 530/329 |
| 4,591,505 | 5/1986 | Prince | 424/101 |
| 4,613,501 | 9/1986 | Horowitz | 424/89 |
| 4,626,524 | 12/1986 | Server | 514/17 |
| 4,644,055 | 2/1987 | Kettner et al. | 530/330 |
| 4,719,177 | 1/1988 | Baltimore et al. | 435/91 |
| 4,742,046 | 5/1988 | Bliah | 514/888 |
| 4,782,135 | 11/1988 | Rinehart, Jr. | 530/317 |
| 4,789,545 | 12/1988 | Woods et al. | 424/89 |

OTHER PUBLICATIONS

Cohen, Science 205, 964–971 (1979).
Dolin, Science 227, 1296–1303 (1985).
Robins, Chem. & Eng. News 64, 28–40 (1986).
Hirsch & Kaplan, Scient. Amer. 256(4), 76–85 (1987).
Varmus, Science 240, 1427–1435 (1988).
Strauss et al., Virology 132, 92–110 (1984).
Schlesinger & Schlesinger, The Togaviridae and Flaviviridae,) Plenium Press, N.Y., 1986, pp. 35–43.
Schlesinger & Cahill, Virology, 168, 187–190 (1989).

Primary Examiner—Lester L. Lee
Attorney, Agent, or Firm—Scott J. Meyer; James W. Williams, Jr.

[57] ABSTRACT

Novel antiviral peptides are disclosed which have a sequence of about 4 to 10 amino acids and which are substantially identical to a small portion of the cytoplasmic domain of a glycoprotein in a virus that contains a lipid-bilayer in its structure.

11 Claims, 1 Drawing Sheet

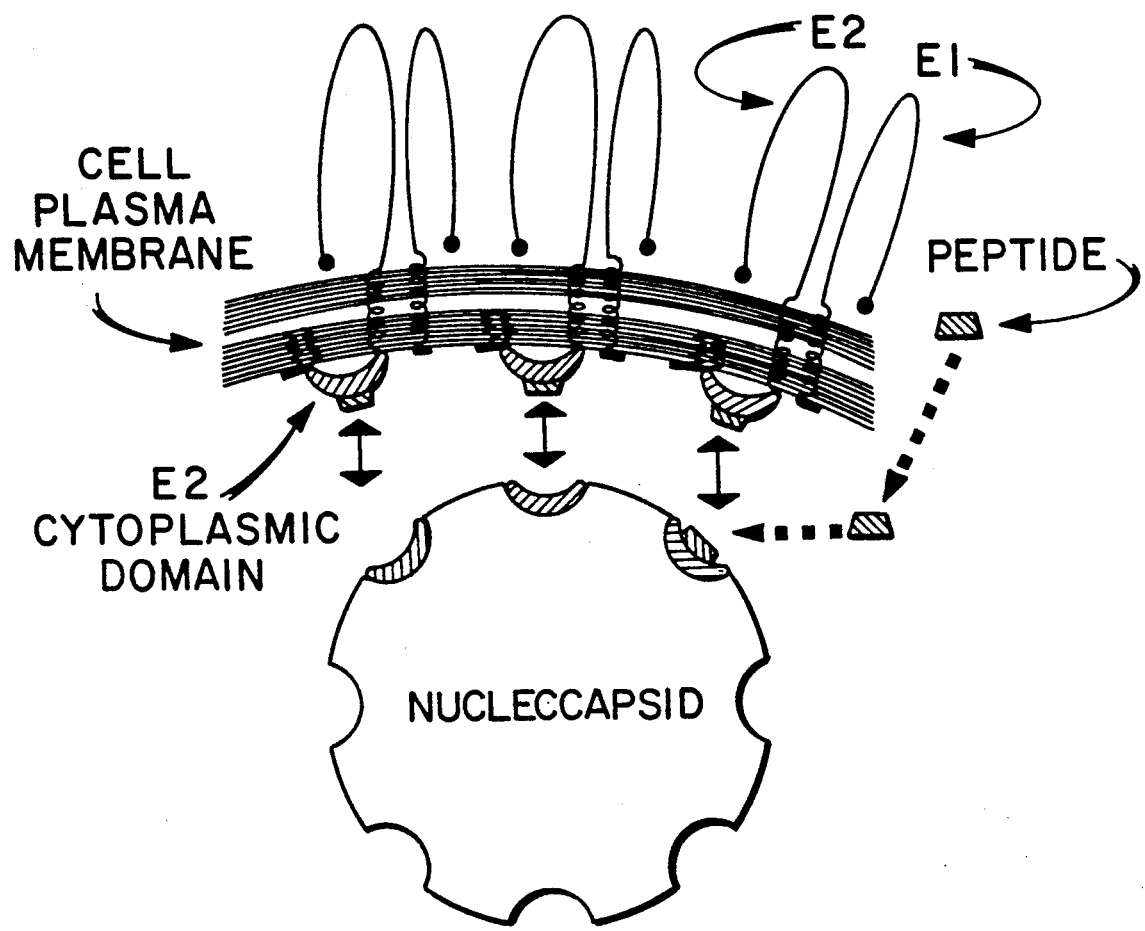

ANTIVIRAL PEPTIDES

This invention relates to novel antiviral peptides and, more particularly, to small peptides which interfere with the final stages of virus intracellular replication.

Although powerful chemotherapeutic agents have been developed for successful treatment of bacterial infections, e.g. the penicillins and cephalosporins, no such comparable antiviral therapies have been devised. Despite the vast number of compounds screened in the past several decades and the multi-millions of dollars spent on development, only a handful of drugs have had limited clinical utility in controlling viral infections. Among the types of compounds having been found to have limited success, the following are illustrative:

Aminoquinolines, e.g. chloroquin (U.S. Pat. No. 2,233,970);
Amantadine (U.S. Pat. No. 3,310,469);
Phosphonoacetic acid or PAA (U.S. Pat. No. 3,767,795);
Phosphonoformic acid (U.S. Pat. No. 4,771,041);
Purine and pyrimidine nucleosides, e.g. 9-$\beta$-D-arabinofuranosyladenine (vidarabine or ara-A, U.S. Pat. No. 3,616,208);
AraH$_x$MP (U.S. Pat. No. 4,093,714);
2'-Deoxy-5-iodouridine (idoxuridine or IDU) and derivatives (U.S. Pat. No. 4,000,260);
Ribavirin (U.S. Pat. No. 3,798,209);
Acyclovir and derivatives (U.S. Pat. No. 4,199,574);
3'-Azido-3'-deoxythym-idine (azidothymidine or AZT) (U.S. Pat. No. 4,724,233).

A significant problem that exists with the analogs of pyrimidines and purines is that they are most often as toxic to an uninfected cell as to virus multiplication in that cell.

Any attempt to treat a viral infection must take into account the various methods by which the virus interacts with the host cell. Viruses consist of a shell of protein enclosing a core of nucleic acid, either ribonucleic acid (RNA) or deoxyribonucleic acid (DNA), that codes for viral reproduction. That is, the RNA or DNA is the genetic material which carries the genes specifying the enzymes and structural proteins that the virus needs to interact with the host cell and reproduce itself. This protein shell also serves as a protective coat to keep the nucleic acid intact and prevent enzymic destruction. Some viruses also contain, in addition to their protein coat, an outer covering referred to as an envelope. This envelope consists of a lipid bilayer which is derived from membranes of the cell in which the virus has replicated and glycoproteins whose sequences are encoded in the virus genome. The structure of these glycoproteins consists of an outer, extra-cellular domain, a transmembranal domain and a cytoplasmic domain which is localized to the interior of the lipid bilayer. Current antiviral therapy thus has attempted to exploit the subtle molecular contrasts between virus and host and to develop antiviral compounds that will interfere with biochemically defined virus-specific functions. See, for example, Cohen, *Science* 205, 964–971 (1979); Dolin, *Science* 227, 1296–1303 (1985); Robins, *Chem. & Eng. News* 64, 28–40 (1986); Hirsch and Kaplan, *Scientific Amer.* 256(4), 76–85 (1987); and Varmus, *Science* 240 1427–1435 (1988).

BRIEF DESCRIPTION OF THE INVENTION

The present invention relates to small novel antiviral peptides which interfere with the final stages of virus intracellular replication. These novel peptides contain sequences of about 4 to 10 amino acids which are substantially identical to a portion of the cytoplasmic domain of a viral glycoprotein in those viruses that contain a lipidbilayer in their structure.

The cytoplasmic domain of the glycoprotein is recognized by the virus intracellular nucleocapsid or matrix protein, and a binding of the latter to the glycoprotein occurs during the final assembly of the virus. Extracellular virions must contain lipid and embedded glycoproteins in order to reinfect other cells in an organism and cause disease. The sequences of the small peptide inhibitors of this invention are unique in that they have sequences substantially identical to a domain in the glycoprotein which participates in binding. They should not have an effect on uninfected host cells.

In a preferred embodiment of the invention, the antiviral peptide is identical to a small portion of the cytoplasmic domain of Sindbis E2 glycoprotein and most preferably is a hexapeptide with the sequence L-T-P-Y-A-L or a heptapeptide with the sequence L-T-P-Y-A-L-A.

In accordance with another embodiment of the invention, the foregoing novel peptides containing unique sequences of about 4 to 10 amino acids which are substantially identical to a small portion of the viral cytoplasmic domain can be provided with enhanced antiviral activity by modifying the N-terminus with an acyl group having from 2 to about 12 carbon atoms, preferably octanoyl.

In a most preferred embodiment of the invention, addition of an octanoyl group to the amno-terminal leucine of a preferred Sindbis virus inhibitory peptide, L-T-P-Y-A-L-A, increased the inhibitory potency 10 fold. When tested on tissue culture cells, this peptide was specific for two non-alphaviruses, Sindbis and Semliki Forest. It had no effect on uninfected cells or on cells infected with a non-alphavirus, viz. a rhabdovirus (vescular stormatitis virus).

It should be understood that variations in the individual amino acids of the peptides or in their end groups which do not adversely or detrimentally affect the desired biological activity as defined herein are included within the scope of the invention. For example, conversion of the peptides into the peptide amide form is a useful variation for antiviral activity.

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments taken in conjunction with the accompanying drawing in which:

FIG. 1 is a schematic which shows the initiation of Sindbis virus assembly, including the host cell plasma membrane, the virus nucleocapsid, the cytoplasmic domain of glycoprotein E2, and the application of an antiviral peptide (blocking peptide) in one embodiment of the invention.

The novel antiviral peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCL in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

The acyl group on the N-terminus is conveniently introduced by reaction of an alkanoic anhydride with the peptide on the solid support after deprotection with TFA.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins, 1 Vol.* 2, p. 255 et seq. (ed. Neurath and Hill), Academic Press, New York, 1976.

The invention is generally applicable to those viruses having so-called envelopes or lipid-bilayers in their structure. Most such viruses are RNA viruses and are exemplified by the alphaviruses in the family Togaviridae such as Sindbis virus and Semiliki Forest virus, retroviruses such as the human immunodeficiency virus (HIV) and human T-cell leukemia virus (HTLV), influenza viruses, respiratory synctial viruses, rabies virus, and flaviviruses such as dengue virus and yellow fever virus. An example of an enveloped DNA virus is the herpes virus.

The invention is particularly adapted to blocking the growth and spread of alphaviruses. Alphaviruses are small, lipid-containing viruses that infect insects and vertebrates. There are about 25 members in the alphavirus genus and they include, in addition to the two mentioned above, the Western, Eastern and Venezuelen equine encephalitis viruses which are pathogenic to horses and humans. Other strains are known to cause fever and acute polyarthritis in man and encephalitis in young children. Background information on these and other such related virus can be had by reference to the recent text by S. Schlesinger and M. Schlesinger, *The Togaviridae and Flaviviridae*, Plenum Press, New York and London, 1986.

In order to illustrate the invention in greater detail, a group of small peptides were synthesized such as to be substantially identical to small portions of the cytoplasmic domain of the Sindbis E2 glycoprotein. The complete nucleotide sequence of the genomic RNA of Sindbis virus and the derived amino acid sequence of E2 are disclosed by Strauss et al., *Virology* 132 92–110 (1984), and in Chapter 3, by E. Strauss and J. Strauss, of the Schlesinger text, supra. The E2 glycoprotein is 423 amino acids long. E2 is formed from a polyprotein; its sequence is found in amino acids 329-751 of the polyprotein in which the first methionine is designated +1.

The cytoplasmic domain of the E2 glycoprotein is a 33 amino acid peptide stretch comprising the C-terminal amino acids 390-423 (corresponding to 719-751 in the aforesaid polyprotein). The cytoplasmic domain of the Sindbis E2 glycoprotein thus has the following amino acid sequence, reading from the amino terminus to the carboxy terminus:

```
390            400                410                420
K—A—R—R—E—C—L—T—P—Y—A—L—A—P—N—A—V—I—P—T—S—L—A—L—L—C—C—V—R—S—A—N—A
```

Various peptides corresponding identically to small portions of the foregoing cytoplasmic domain were synthesized in the peptide amide form by standard solid-phase peptide synthesis. The synthesized peptides were then tested as inhibitors of Sindbis virus replication (or Semliki virus in one test) in chicken embryo fibroblasts by the method described by Schlesinger and Cahill, *Virology* 168, 187–190 (1989). According to this method, replication of the virus in the presence and absence of the test peptide was measured by quantitating both the release of radioactive particles into the tissue culture medium and the amounts of radioactive virus nucleocapsids and glycoproteins remaining inside the infected cells. The test peptide at a final concentration of 0.1 mg/ml was added 3 hours post infection. Virus release was measured by isolating particles from the media of infected and [$^{35}$S]methionine-labeled chicken embryo fibroblasts and determining the amounts of [$^{35}$S]methionine incorporated into virus-specific proteins separated by sodium dodecylsulfate polyacrylamide gel electrophoresis (SDS-PAGE). The ratio of extracellular virus to intracellular virus proteins was calculated and expressed in percentages to represent the degree of inhibition.

In accordance with the foregoing assay, the most effective peptide was a hexapeptide amide of the following amino acid sequence:

L-T-P-Y-A-L.

This peptide corresponds to amino acids 397–402 in the E2 glycoprotein of the Sindbis virus. This hexapeptide is also present in the E2 glycoprotein of Eastern equine encephalitise virus [Chang and Trent, *J. Gen. Virol.* 68, 2129 (1987)] and Ross river virus [Dalgarno et al., *Virology* 129, 170 (1983)].

Other peptides corresponding to portions of the Sindbis E2 glycoprotein have been synthesized in the peptide amide form with amino acid sequences as follows:

K—A—R—R—E—C—L—T—P—Y—A—L—A—P—N—A—V—I—P—T—S—L—A*
R—E—C—L—T—P—Y—A—L—A—P—N—A—V—I—P—T—S—L—A*
K—A—R—R—E—C—L—T—P*
K—A—R—R—E—C
A—L—A—P—N—A
V—I—P—T—S—L
Y—A—L—A—P—N—A—V—I—P—T—S—L—A—L—L
N—A—V—I—P—T—S—L—A—L—L
P—T—S—L—A—L—L.

The three peptides indicated with an asterisk showed some inhibitory effect on virus release in the above assay; whereas, the other peptides were inactive.

The inhibitory enhancement of the small peptides of the invention by acylation of the N-terminus is illustrated by octanoylation of the heptapeptide amide having the following amino acid sequence:

L-T-P-Y-A-L-A.

The octanoyl group on the N-terminal leucine of the heptapeptide was introduced by reaction of octanoic anhydride with the peptide on the solid support that had been deprotected with TFA. Confirmation of the structure of the purified octanoyl heptapeptide was made by mass spectrometry. The antiviral results with the foregoing hexapeptide amide and the octanoylated heptapeptide amide are set forth in Tables I and II, respectively. In Test 3 of Table I, the test virus was Semliki Forest virus; whereas, Sindbis virus was used in replicate Tests 1 and 2 of Table I and replicate Tests 1, 2 and 3 of Table II.

TABLE I

INHIBITION OF SINDBIS VIRUS RELEASE
BY HEXAPEPTIDE L-T-P-Y-A-L[a]

| Test | | Ratio of Extracellular Virus to Intracellular Virus Proteins | |
|---|---|---|---|
| 1. | Peptide | .15 | (70%)[b] |
| | None | .46 | |
| 2. | Peptide | .08 | (50%) |
| | None | .16 | |
| 3. | Peptide | .20 | (36%)[c] |
| | None | .31 | |

[a]Peptide (1.0 mg/ml final level) was added 3 hr post infection with [35S]methionine. Virus and cells were collected 3 hr later.
[b]Degree of Inhibition
[c]Semliki Forest Virus Inhibition in Test 3.
Note:
1. There was no inhibition of intracellular virus protein synthesis by the peptide at this level.
2. There was no inhibition of vesicular stomatitis virus formation and secretion by the peptide at this level.

TABLE II

INHIBITION OF SINDBIS VIRUS RELEASE
BY OCTANOLYLATED HEPTAPEPTIDE L-T-P-Y-A-L-A[a]

| Test | | Ratio of Extracellular Virus to Intracellular Virus Proteins | |
|---|---|---|---|
| 1 | Peptide | .10 | (60%)[b] |
| | None | .25 | |
| 2. | Peptide | .27 | (50%) |
| | None | .56 | |
| 3. | Peptide | .19 | (50%) |
| | None | .36 | |

[a]Peptide (0.1 mg/ml final level) was added 3 hr post infection with [35S]methionine. Virus and cells were collected 3 hr later.
[b]Degree of Inhibition.
Note:
1. There was no inhibition of intracellular virus protein synthesis by the peptide at this level.
2. There was no inhibition of vesicular stomatitis virus formation and secretion by the peptide at this level.

Other glycoproteins of viruses that contain a lipid-bilayer in their structure from which small antiviral peptides can be derived in accordance with the invention are, for example, the following:

Human immunodeficiency virus (glycoprotein GP41);
Influenza viruses (hemagglutinin glycoprotein-HA2);
Respiratory synctial viruses ("G" glycoprotein);
Rabies virus ("G" glycoprotein);
Dengue virus ("E" protein); and
Herpes viruses (gB and gD glycoproteins).

Amino acids are shown herein by standard one letter abbreviations as follows:

| Abbreviated Designation | Amino Acid |
|---|---|
| A | Alanine |
| C | Cysteine |
| D | Aspartic acid |
| E | Glutamic acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |

Various other examples will be apparent to the person skilled in the art after reading the present disclosure without departing from the spirit and scope of the invention. It is intended that all such other examples be included within the scope of the appended claims.

What is claimed is:

1. An antiviral peptide having a sequence of about 4 to 10 amino acids which is substantially identical to a small portion of the cytoplasmic domain of a glycoprotein in Sindbis virus.

2. An antiviral peptide having a sequence of about 4 to 10 amino acids which is substantially identical to a small portion of the cytoplasmic domain of a glycoprotein in Semliki Forest virus.

3. The peptide of claim 3 having the amino acid sequence.

L-T-P-Y-A-L.

4. The peptide of claim 3 having the amino acid sequence.

L-T-P-Y-A-L-A.

5. The peptide of claim 4 having its amino terminus substituted with octanoyl.

6. The method of inhibiting viral intracellular replication of Sindbis virus comprising subjecting said virus to an inhibitory effective amount of a peptide having a sequence of about 4 to 10 amino acids which is substantially identical to a small portion of the cytoplasmic domain of a glycoprotein in said virus.

7. The method of inhibiting viral intracellular replication of Semliki Forest virus comprising subjecting said virus to an inhibitory effective amount of a peptide having a sequence of about 4 to 10 amino acids which is substantially identical to a small portion of the cytoplasmic domain of a glycoprotein in said virus.

8. The method of claim 6 having the amino acid sequence
L-T-P-Y-A-L.

9. The method of claim 6 having the amino acid sequence
L-T-P-Y-A-L-A.

10. The method of claim 9 having its amino terminus substituted with octanoyl.

11. The method of claim 6 in which the glycoprotein is the E2 glycoprotein of Sindbis virus.

* * * * *